(12) United States Patent
Garg et al.

(10) Patent No.: US 6,846,959 B2
(45) Date of Patent: Jan. 25, 2005

(54) PROCESS FOR PRODUCING ALKANOLAMINES

(75) Inventors: Diwakar Garg, Emmaus, PA (US); Shashank Navin Shah, Allentown, PA (US); Matthew Joseph Okasinski, Harleysville, PA (US); Ava S. Drayton-Elder, Orefield, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 306 days.

(21) Appl. No.: 10/266,958

(22) Filed: Oct. 7, 2002

(65) Prior Publication Data

US 2004/0068143 A1 Apr. 8, 2004

(51) Int. Cl.$^7$ .............................................. C07C 213/04
(52) U.S. Cl. ...................... 564/475; 564/477; 564/497; 564/499
(58) Field of Search ................................. 564/475, 477, 564/497, 499

(56) References Cited

U.S. PATENT DOCUMENTS

| | | | |
|---|---|---|---|
| 2,337,004 A | 12/1943 | Schwoegler ................. 260/584 |
| 3,131,132 A | 4/1964 | Moss et al. .................... 202/57 |
| 4,443,559 A | 4/1984 | Smith, Jr. .................... 502/527 |
| 4,504,687 A | 3/1985 | Jones, Jr. .................... 568/697 |
| 4,567,303 A | 1/1986 | Boettger et al. ............. 564/475 |
| 4,935,577 A | 6/1990 | Huss, Jr. et al. ............. 585/726 |
| 4,950,834 A | 8/1990 | Arganbright et al. ....... 585/446 |
| 4,978,807 A | 12/1990 | Smith, Jr. .................... 568/697 |
| 5,043,506 A | 8/1991 | Crossland ................... 585/449 |
| 5,057,468 A | 10/1991 | Adams .......................... 502/1 |
| 5,086,193 A | 2/1992 | Sy ............................... 585/446 |
| 5,108,550 A | 4/1992 | Pinaire et al. ................. 203/1 |
| 5,130,102 A | 7/1992 | Jones, Jr. .................... 422/191 |
| 5,189,001 A | 2/1993 | Johnson ...................... 502/159 |
| 5,196,612 A | 3/1993 | Ward ........................... 568/697 |
| 5,221,441 A | 6/1993 | Smith, Jr. ..................... 203/29 |
| 5,235,102 A | 8/1993 | Palmer et al. ............... 562/607 |
| 5,243,102 A | 9/1993 | Marker et al. .............. 568/697 |
| 5,248,837 A | 9/1993 | Smith, Jr. et al. ........... 568/697 |
| 5,258,560 A | 11/1993 | Marker ....................... 568/697 |
| 5,262,012 A | 11/1993 | Smith, Jr. .................... 202/158 |
| 5,266,546 A | 11/1993 | Hearn ......................... 502/300 |
| 5,291,989 A | 3/1994 | Pinaire et al. ............... 202/158 |
| 5,308,451 A | 5/1994 | Carland ....................... 202/158 |
| 5,321,163 A | 6/1994 | Hickey et al. ................. 568/59 |
| 5,336,841 A | 8/1994 | Adams ......................... 585/834 |
| 5,338,517 A | 8/1994 | Evans, III et al. ........... 422/191 |
| 5,348,710 A | 9/1994 | Johnson et al. ............. 422/211 |
| 5,395,981 A | 3/1995 | Marker ....................... 568/697 |
| 5,431,890 A | 6/1995 | Crossland et al. .......... 422/211 |
| 5,449,501 A | 9/1995 | Luebke et al. .............. 422/193 |
| 5,454,913 A | 10/1995 | Yeoman et al. ............... 203/29 |
| 5,463,134 A | 10/1995 | Frey ............................. 568/59 |
| 5,476,978 A | 12/1995 | Smith, Jr. et al. ........... 585/323 |
| 5,496,446 A | 3/1996 | Yeoman et al. ............. 202/158 |
| 5,504,258 A | 4/1996 | Marker et al. .............. 565/695 |
| 5,510,568 A | 4/1996 | Hearn ......................... 585/834 |
| 5,516,955 A | 5/1996 | Gentry ........................ 585/477 |
| 5,523,062 A | 6/1996 | Hearn et al. ................. 422/195 |
| 5,536,886 A | 7/1996 | Tamminen et al. ......... 568/697 |
| 5,593,548 A | 1/1997 | Yoeman et al. ............... 203/29 |
| 5,597,476 A | 1/1997 | Hearn et al. ................. 208/208 |
| 5,599,997 A | 2/1997 | Hearn et al. ................. 564/450 |
| 5,601,797 A | 2/1997 | Gentry ........................ 423/659 |
| 5,659,106 A | 8/1997 | Frey et al. ................... 585/803 |
| 5,663,444 A | 9/1997 | Melder et al. ............... 564/477 |
| 5,679,241 A | 10/1997 | Stanley et al. ............... 208/92 |
| 5,679,862 A | 10/1997 | Nemphos et al. ........... 564/480 |
| 5,730,843 A | 3/1998 | Groten et al. ............... 202/158 |
| 5,744,645 A | 4/1998 | Marker et al. .............. 565/695 |
| 5,779,993 A | 7/1998 | Gentry ........................ 422/191 |
| 5,792,428 A | 8/1998 | Bakshi et al. ............... 422/112 |
| 5,847,249 A | 12/1998 | Maraschino ................ 585/259 |
| 5,855,741 A | 1/1999 | Koch et al. .................. 202/158 |
| 5,863,419 A | 1/1999 | Huff, Jr. et al. ............. 208/237 |
| 5,942,456 A | 8/1999 | Crossland et al. ............. 502/2 |
| 6,008,416 A | 12/1999 | Lawson et al. ............. 568/396 |
| 6,075,168 A | 6/2000 | DiGuilio et al. ............ 564/487 |
| 6,084,141 A | 7/2000 | Mikitenko et al. .......... 585/263 |
| 6,696,610 B2 * | 2/2004 | Peschel et al. .............. 564/463 |

FOREIGN PATENT DOCUMENTS

| | | |
|---|---|---|
| EP | 0919537 | 8/2003 |
| JP | 9020733 | 1/1997 |
| RU | 2162461 | 1/2001 |
| WO | WO 9733953 | 9/1997 |
| WO | WO 9809929 | 3/1998 |
| WO | WO 9825696 | 6/1998 |
| WO | WO 0026178 | 10/1998 |
| WO | WO 9832510 | 11/1998 |
| WO | WO 0032553 | 6/2000 |
| WO | WO 0153250 | 7/2001 |
| ZA | 0950015 | 2/2003 |

OTHER PUBLICATIONS

Brzozowski, et al., "Technologia Chemiczna na Przelomie Wiekow," Publisher: Wydawnictwo Stalego Komitetu Kongresow Technologil Chemicznej, Gliwice, 2000, pp. 223–226. (Abstract).

* cited by examiner

*Primary Examiner*—Brian J. Davis
(74) *Attorney, Agent, or Firm*—Michael Leach

(57) ABSTRACT

A process for producing an alkanolamine includes supplying a reactive distillation apparatus having an inner contacting surface which simultaneously facilitates a reaction process and a distillation process, feeding a first reactant including an amine represented by $R'_{3-x}NH_x$, wherein R' is a hydrocarbon group, and X is 1, 2, or 3, feeding a second reactant including an akylene oxide represented by R"O, wherein R" is a $C_2$–$C_{10}$-alkylene, feeding a catalyst in an amount from 0% to about 15% by weight of a mixture of the first reactant, the second reactant and the catalyst; recycling an overhead output from an overhead portion including an unreacted portion of the amine and the catalyst to achieve a substantially total reflux of the amine and the catalyst, and collecting a product output including an alkanolamine, the alkanolamine being a member selected from the group consisting of a monoalkanolamine, a dialkanolamine, and a trialkanolamine.

32 Claims, 2 Drawing Sheets

PROCESS FOR PRODUCING ALKANOLAMINES

BACKGROUND OF THE INVENTION

This invention relates to a process for producing alkanolamines. Alkanolamines are valuable chemicals, which have applications as final or intermediate products in many industries such as pharmaceutical, chemical, petrochemical, etc.

Alkanolamines are routinely produced by reacting an alkylene oxide with an amine. The process is generally carried out in two distinct steps, wherein a reaction step is carried out in a reactor followed by a purification step, which is performed in a distillation column. There are two types of reaction of an alkylene oxide with an amine known in the prior art: an aqueous phase reaction and a non-aqueous phase reaction. The aqueous phase reaction, which is usually very fast, is carried out at low temperatures (usually less than 100° C.) by using water as a catalyst. The non-aqueous phase reaction is carried out at higher temperatures (usually greater than 100° C.) in the absence of water but in the presence of a product, which acts as a catalyst. A separate step to remove water from the product is required when water is used as a catalyst, making the overall process a three-step process.

There is a variety of processes commonly used for producing alkanolamines, wherein an alkylene oxide is reacted with primary or secondary amines. These processes comprise a step of reacting an alkylene oxide with an amine in a reactor followed by a step of distilling the reactor's effluent to recover and purify the desired alkanolamine. For example, U.S. Pat. No. 2,337,004 to Schwoegler describes a two-step non-aqueous phase process for producing alkanolamine. The two-step process involves (1) reacting an amine with an anhydrous alkylene oxide in a reactor and (2) recovering the product alkanolamine by distillation.

U.S. Pat. No. 3,131,132 to Moss et al. and U.S. Pat. No. 5,663,444 to Melder et al. describe two-step aqueous phase processes for producing alkanolamine. These two-step processes also involve (1) reacting an amine with an anhydrous alkylene oxide in a reactor and (2) recovering the product alkanolamine by distillation. See also U.S. Pat. No. 4,567,303 to Boettger et al.

Finally, European Patent EP 0919537 and Japanese Patent JP 09020733 describe two-step aqueous phase processes for producing an alkanolamine having a desired color. The disclosed two-step processes involve (1) reacting an amine with an alkylene oxide in an aqueous phase in a reactor and (2) recovering the product alkanolamine by distillation.

Although we are aware of patents describing reactive distillation reactors and structures, we have not located art that describes production of alkanolamines from alkylene oxide and primary or secondary alkylamines by a reactive distillation process.

U.S. Pat. No. 6,075,168 to DiGuilio et al. describes a reactive distillation process for producing dialkanolamine from alkylene oxide and monoalkanolamine or a mixture of mono, di, and tri alkanolamines. This patent teaches the use of an alkanolamine feed stream rather than using ammonia or alkylamines. Even though a broad range of pressures is disclosed, the examples disclose a process conducted at a low pressure or vacuum to facilitate volatilization and stripping of alkanolamine in the reactive distillation column (see column 4, lines 24–27). The low pressure is used in this process because alkanolamines, in general, are less volatile than ammonia, primary amines, or alkylamines. The disclosed process does not teach the use of a catalyst such as water or a product alkanolamine to facilitate the reaction. In this process, the alkanolamine is used as a feedstock or a reactant.

The following U.S. Pat. Nos. 4,443,559; 5,057,468; 5,108,550; 5,130,102; 5,189,001; 5,221,441; 5,235,102; 5,262,012; 5,266,546; 5,291,989; 5,308,451; 5,348,710; 5,338,517; 5,431,890; 5,454,913; 5,449,501; 5,496,446; 5,504,258; 5,523,062; 5,593,548; 5,942,456; 5,601,797; 5,730,843; 5,779,993; 5,792,428; 5,847,249; 5,855,741; and 5,942,456; and PCT published applications WO 98/25696; WO 98/32510; and WO 00/26178 and South African Patent No. 950015 generally describe catalytic distillation apparatuses and methods, a liquid phase catalyst assembly for a chemical process tower, and/or an apparatus for conducting exothermic reactions. However, these patents do not disclose the production of alkanolamines from alkylene oxide and primary or secondary amines by reactive distillation process.

U.S. Pat. Nos. 4,504,687; 4,978,807; 5,196,612; 5,243,102; 5,248,837; 5,258,560; 5,321,163; 5,395,981; 5,504,258; 5,536,886; 5,744,645; and 6,008,416 describe a variety of processes for producing ethers and ketones using a reactive or a catalytic distillation. U.S. Pat. Nos. 4,935,577; 4,950,834; 5,043,506; 5,086,193; 5,476,978; and PCT published application WO 98/09929 describe a variety of processes for alkylation of aromatic compounds using reactive or catalytic distillation.

U.S. Pat. Nos. 5,463,134; 5,510,568; 5,597,476; 5,659,106; 5,863,419 and 5,679,241 describe catalytic distillation processes for removing sulfur and olefins from a variety of hydrocarbon streams. U.S. Pat. No. 5,336,841 to Adams and U.S. Pat. No. 5,516,955 to Gentry describe processes for processing and separating hydrocarbons by catalytic distillation. PCT published application WO 97/33953 describes a process for hydrogenating heavy unsaturates in an olefins plant by catalytic distillation. U.S. Pat. No. 6,084,141 to Mikitenko et al. describes a process for selective hydrogenation of light unsaturated hydrocarbons. These patents do not disclose the production of alkanolamines from alkylene oxide and primary or secondary amines by reactive distillation process.

U.S. Pat. No. 5,679,862 to Nemphos et al. discloses a catalytic distillation process for aminating aliphatic alkane derivatives in the presence of hydrogen and ammonia. U.S. Pat. No. 5,599,997 to Hearn et al. describes a catalytic distillation process for producing a cyclohexyl amine by hydrogenation of aniline.

Russian Patent RU 2162461 to Ryleev et al. discloses a process of producing ethanolamines by reacting ethylene oxide and anhydrous ammonia in the presence of monoethanolamine with in-process recycling of a liquid-phase ammonia. When an ammonia:ethylene oxide :monoethanolamine molar ratio reaches 20–30:1:1.5, the excess of the ammonia is removed from the reaction mixture by a distillation at 15–35 atm until the ammonia content is approximately 11 molar %. The rest of the ammonia is removed by an evaporation at 140–165° C. and 14–16 atm, followed by desorption at 160–165° C. and 2–4 atm, and absorption by monoethanolamine. The resulting absorbate, which contains approximately 6 molar % of ammonia, is returned into the initial reaction mixture. Monoethanolamine, diethanolamine and triethanolamine are recovered by known techniques. The removal of ammonia at 2–4 atm and its absorption with monoethanolamine enable in-process recycling of ammonia in a liquid phase, thus eliminating the need for a compression equipment or special cooling agents and reducing the ammonia content in final products to 0.1% or less.

International publication WO 2001053250 to Brun-Buisson et al. discloses a continuous multicolumn process for producing triethanolamine (TEA) comprising: (i) synthesizing the TEA by continuously bringing ammonia into contact with ethylene oxide under conditions allowing the formation of a reaction mixture comprising mono-, di- and triethanolamines; (ii) continuously separating the ammonia that has not reacted from the reaction mixture; and (iii) continuously separating the TEA from the mixture resulting from step (ii). The process is characterized in that a specific mixture of alkanolamines, comprising TEA and 0.5–50% of at least one secondary dialkanolamine (e.g., diethanolamine), is prepared or isolated from the mixture resulting from step (ii), and in that the TEA is separated and isolated with a degree of purity of ≧99.2% by a continuous distillation of the specific mixture of alkanolamines. The TEA produced is of high purity and has a high resistance to coloration.

An article by Brzozowski et al. (Technologia Chemiczna na Przelomie Wiekow (2000), 223–226 Publisher: Wydawnictwo Stalego Komitetu Kongresow Technologii Chemicznej, Gliwice) discloses that in a nucleophilic substitution reaction involving ammonia, $H_2O$, alcohols or phenols (PhOH) can be used as catalysts. The manufacture of ethanolamines in a waterless environment under high pressure and at high temperature was examined. The reaction can be carried out successfully in the presence of traces of $H_2O$ present in the stream of reactants. When a 10:1 molar ratio of $NH_3$ to ethylene oxide mixture was subjected to a reaction for several minutes at 10 mPa and 150° C., 100% conversion of ethylene oxide was achieved. At higher temperatures, the proportion of $HOCH_2CH_2NH_2$ (MEA) in the products decreased and the proportion of $(HOCH_2CH_2N)_3$ (TEA) increased. The product obtained at 100° C. contained more than 70% MEA and 5% TEA, while at 200° C. it contained 17% MEA, 17% $(HOCH_2CH_2)_2NH$ (DEA) and 63% TEA. A high excess of $NH_3$ restricts side reactions of ethylene oxide and also increases the yield of MEA. The product obtained at a high $NH_3$/ethylene oxide ratio (50–100:1) and a pressure of 15 MPa contained more than 90% MEA.

International publication WO 2000032553 to Ruider et al. discloses producing a crude triethanolamine by a liquid-phase reaction of aqueous ammonia with ethylene oxide under pressure and at an increased temperature, followed by a purification including the steps of: (1) separation of excess ammonia, water, and monoethanolamine from the reaction product, (2) ethoxylation of the separated products at 110–180° with an additional amount of ethylene oxide, and (3) vacuum distillation of the reaction product in the presence of phosphorous acid or hypophosphorous acid.

U.S. Pat. No. 5,663,444 to Melder et al discloses a process for making a color-stable dialkylaminoethanol by reacting ethylene oxide with a dialkylamine in the presence of from 2.5 to 50% by weight of water, based on the reaction mixture, at a temperature of from 95° to 170° C. and separating off the water and high-boiling constituents by distillation under a reduced pressure and at a temperature of from 40° to 90° C. at the bottom of the column.

Accordingly, it is desired to provide a process for producing alkanolamines by reacting an amine with alkylene oxide in the presence or absence of a catalyst in a reactive distillation apparatus.

All references cited herein are incorporated herein by reference in their entireties.

BRIEF SUMMARY OF THE INVENTION

Accordingly, the invention provides a process for producing an alkanolamine, said process comprising:

supplying a reactive distillation apparatus, wherein the reactive distillation apparatus has an inner contacting surface and the inner contacting surface facilitates simultaneously a reaction process and a distillation process;

feeding to the reactive distillation apparatus a first reactant, the first reactant comprising an amine represented by $R'_{3-X}NH_X$, wherein R' is a hydrocarbon group, and X is 1, 2, or 3;

feeding to the reactive distillation apparatus a second reactant, the second reactant comprising an akylene oxide represented R"O, wherein R" is a $C_2$–$C_{10}$-alkylene;

feeding to the reactive distillation apparatus a catalyst, wherein the catalyst is provided in an amount from about 0% to about 15% by weight of a mixture of the first reactant, the second reactant and the catalyst;

recycling an overhead output from an overhead portion of the reactive distillation apparatus, the overhead output comprising an unreacted portion of the amine and the catalyst, wherein the overhead output is returned to the reactive distillation apparatus to achieve a substantially total reflux of the amine and the catalyst; and collecting a product output from a bottom portion of the reactive distillation apparatus, wherein the product output comprises an alkanolamine, the alkanolamine comprising at least one member selected from the group consisting of a monoalkanolamine, a dialkanolamine, and a trialkanolamine.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1:
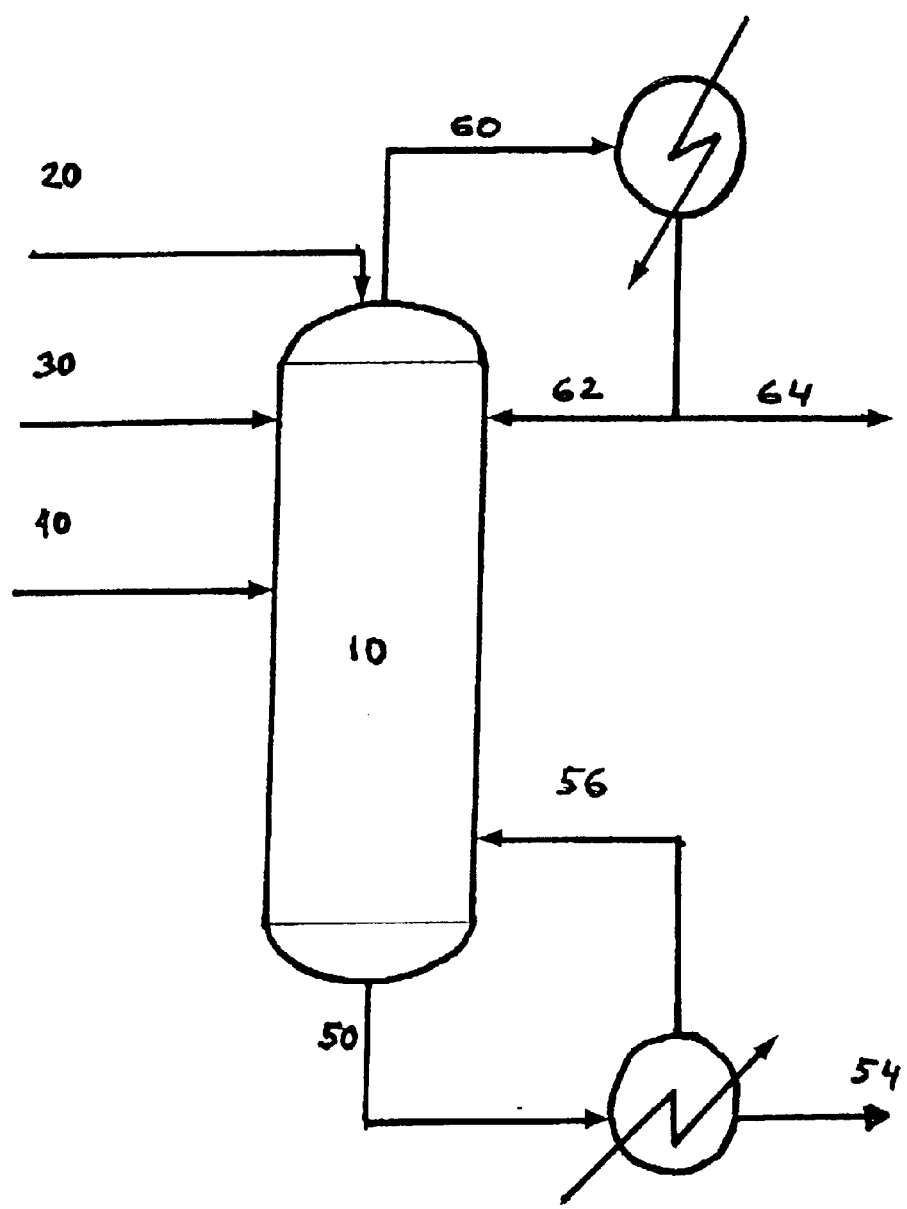
FIG. 1 illustrates a flow diagram for one embodiment of the process of this invention.

The present invention provides a process for producing alkanolamine or a mixture of alkanolamines in a reactive distillation apparatus from an alkylene oxide and an amine in a reactive distillation process. The invention can be practiced over a wide range of processing conditions including but not limited to a feed ratio of reactants, temperature, and pressure. The process of the invention can be conducted in the presence or absence of a catalyst, wherein the catalyst is preferably water or alkanolamine. The process can be conducted in aqueous or non-aqueous phase. A desired output product can be manipulated to contain various ratios of mono-, di- and tri-alkanolamines by selecting appropriate processing conditions.

Advantageously, the present invention provides a one-step reactive distillation process wherein it is proposed to react an alkylene oxide with an amine inside a reactive distillation column and to purify the product alkanolamine at the same time. Combining the reaction and purification steps into one-step provides a unique opportunity to significantly reduce the overall capital requirement and operating cost.

One of reactants contemplated by this invention is an amine, which is represented by a general formula (I):

$$R'_{3-X}NH_X \quad (I)$$

wherein X is 1, 2, or 3, and R' is a hydrocarbon group and isomers thereof which can be an aliphatic, alicyclic or aromatic group preferably a $C_1$–$C_{24}$-alkyl and isomers thereof, more preferably $C_1$–$C_8$-alkyl and isomers thereof, and most preferably $C_1$–$C_4$-alkyl and isomers thereof. In certain embodiments, R' is methyl, ethyl, propyl, isopropyl, butyl, isobutyl, tert-butyl, pentyl, isopentyl, hexyl, octyl or 2-ethylhexyl.

In one embodiment of the invention, when X is 3, the amine is ammonia. In another embodiment of the invention, when X is 1, R' can comprise of either two of same or different $C_1$–$C_{24}$-alkyls. For example, when X is 1, the amine can be a methylethylamine, a dimethylamine, or a diethylamine. Preferred examples of amines of the present invention are monomethylamine, dimethylamine, and diethylamine.

Another reactant contemplated by this invention is an akylene oxide, wherein the akylene oxide is represented by a general formula (II):

$$R''O \quad (II)$$

wherein R'' is a $C_2$–$C_{10}$-alkylene and isomers.

Preferred examples of akylene oxides are ethylene oxide, propylene oxide, butylene oxide, and hexylene oxide.

The output product alkanolamine is represented by a general formula (III):

$$R'_{3-X}NR'''_X \quad (III)$$

wherein X can be 1, 2, or 3 respectively, R' is a hydrocarbon group and isomers thereof, preferably a $C_1$–$C_{24}$-alkyl and isomers thereof as described above, and R''' is a $C_2$–$C_{10}$-alkanol group bearing at least one hydroxyl group.

In one embodiment of the invention, the output product of the process of the present invention is a mixture or a plurality of alkanolamines selected from the group of mono-, di-, and tri-alkanolamines. In another embodiment of the invention, the output product is di-alkanolamine. The preferred alkanolamine is isopropanolamine, ethanolamine, methylethanolamine, dimethylethanolamine, and diethylethanolamine.

The production of a wide variety of alkanolamines using a two-step or a three-step process has been extensively studied by inventors in batch reactors. It was determined that to achieve a high yield of the desired product, alkanolamine or a mixture of alkanolamines, in the two-step process, an excess molar ratio of the amine to the alkylene oxide was required. However, the use of a high amine (or ammonia) to alkylene oxide ratio in the reaction mixture leads to a large amine (or ammonia) recycle and increases the heat load both in the reaction and in the distillation steps, thereby increasing the cost of producing alkanolamines.

Reactive Distillation Process of the Present Invention for Producing Alkanolamines Since the rate of a reaction between an amine and an alkylene oxide is extremely rapid, and there is a substantial difference between the boiling points of the reactants and the boiling point of product alkanolamine, it is desired to utilize these unique properties of the reaction and the reaction products to streamline and economize the production of alkanolamines. Consequently, it is proposed to react an alkylene oxide with an amine inside a reactive distillation column while purifying the product alkanolamine at the same time. Combining the reaction and purification steps into one-step in a reactive distillation process provides a unique opportunity to significantly reduce the overall capital requirement and operating cost. Besides reducing the overall capital requirement and reducing operating cost, the reactive distillation process provides opportunities: (1) to reduce the rise in reaction temperature due to the highly exothermic nature of the reaction, (2) to reduce the formation of undesirable byproducts by balancing the exothermic heat of the reaction with the heat of vaporization of a feed amine and recycling the unreacted portion of the amine internally to provide a high amine to alkylene oxide ratio in the column, and (3) to facilitate the production of high quality alkanolamine or a mixture of alkanolamines in which byproduct impurities are greatly reduced without using an excessive ratio of amine to alkylene oxide in the feed and without increasing the energy demand.

The design of a reactive distillation unit for producing high quality alkanolamine depends primarily upon the temperature stability of the product alkanolamine and the phase of the reaction, i.e., an aqueous phase or in a non-aqueous (or an anhydrous) phase. These two important factors dictate processing parameters of a reactive distillation apparatus including but not limited to operating pressure, desired temperature profile in the column, reflux and boilup (or reboiler) rates from a condenser and a reboiler, number of distillation trays or stages required for the reaction and the product separation, and locations of introducing fresh amine (or ammonia) and alkylene oxide feeds to the reactive distillation apparatus.

While operating conditions can be determined by persons skilled in the art using this disclosure as a guide, preferred conditions can be summarized as follows:

operating pressure is about 0.1 bar to about 100 bar (about 0.1 kPa to about 100 kPa) and more preferably about 1 bar to about 100 bar; and reaction temperature is about 305° K to about 573° K.

The reactive distillation apparatus used for performing the reaction and the distillation simultaneously is preferably a tower having an overhead portion, a top portion and a bottom portion, more preferably a column. The particular type of tower employed is not critical, and many conventional columns can be used. The reactive distillation column can be comprised of a reaction zone, preferably located in the top portion.

The reactive distillation apparatus can have an inner contacting surface consisting of one or more distillation trays to facilitate the reaction. Alternatively, it can consist of structural packing or dumped packing instead of trays to facilitate the reaction. Preferred packing material is a material supplied by Koch Engineering Company Inc., Norton and Sulzer Chemtech USA, as disclosed in U.S. Pat. No. 6,075,168. Preferred examples of packing materials are ceramics, fiber glass, stainless steel, carbon steel, nickel-based alloys such as HASTELLOY, MONEL, aluminium, copper-bronze alloys, brass, titanium, nickel, and plastic such as polypropylene (PP), polyvinylidene fluoride (PVDF), fluoropolymer fiber (e.g., Teflon), and polyurethane foam (PFA).

The column can alternatively be packed with catalytic packing materials known in the prior art and similar to those mentioned in numerous patents cited above. Preferred example of the catalytic packing material is KATAPAK made by Sulzer Chemtech. However, the packing material and structural packing can be without a catalyst and consist of inert metallic or ceramic materials.

In the process of the invention, reactants are fed continuously and separately to the column at one or more feed points located on the column, wherein they are intensively mixed with the reactants already present in the column. The mixing is provided by the methods known in the art. Preferably, the reactants are fed to the reaction zone in the column. Each reactant can be fed to one or more feed points located on the column. The location of the feed point or points of one reactant can vary in relation to the location of the feed point or points of another reactant.

The present invention can be conducted in aqueous or non-aqueous phases.

In one embodiment of the present invention, alkanolamine or a mixture of the alkanolamines is produced in a reactive distillation column by reacting reactants such as an amine, e.g., ammonia, and an alkylene oxide in the presence of water as a catalyst to form a desired product alkanolamine. Preferably, catalyst is provided in an amount from about 0% to about 15% by weight of a mixture of the ammonia, the alkylene oxide and the catalyst. The output product alkanolamine can be manipulated to contain various ratios of mono-, di- and trialkanolamines by selecting appropriate processing conditions. In one embodiment of the invention, the output product of the process of the present invention is a plurality of alkanolamines selected from the group of mono-, di-, and trialkanolamines. In another embodiment of the invention, the output product of the process of the present invention is dialkanolamine.

This process is illustrated in FIG. 1, wherein a first reactant, preferably an amine, is fed to the column 10 via line 30 and a second reactant, preferably alkylene oxide, is fed to the column 10 via line 40. Both reactants can be fed at more than one feed point in the column. Also, the position of one reactant in relation to another reactant can be switched in that the alkylene oxide can be fed at a location above the amine. The distance between the feed points can also vary and affects the molar ratio of desired alkanolamines. Preferably, the reactants, the amine and the alkylene oxide are fed to the column at an initial molar ratio of the amine to the alkylene oxide from about 0.1:1 to 1.1:1, wherein the initial molar ratio is measured outside of the reactive distillation apparatus. As explained in detail below, a process molar ratio of reactants, that is the molar ratio of reactants measured inside the column, is higher than the initial ratio due to recycling an unreacted portion of the reactants.

Water is introduced via line 20 to the overhead portion of the column 10. The reaction occurs in a liquid phase, wherein the desired product alkanolamine is produced and the unreacted portion of reactants and water are refluxed or recycled back to the column. Close to a total reflux is achieved when water, the unreacted amine, and alkylene oxide (if any) are removed in a gaseous state via line 60, condensed and returned to the column via line 62. Preferably, due to the total reflux, the process molar ratio of the amine to the alkylene oxide ranges from about 1.1:1 to about 300:1, and more preferably from about 5:1 to about 200:1, wherein the process molar ratio is measured inside of the reactive distillation apparatus. An optional purge line 64 is provided to regulate the reflux.

The desired product alkanolamine travels through the distillation zone of the column 10 and is removed from the column 10 via line 50 to a reboiler. A portion of the product alkanolamine can be reboiled and returned back to the distillation zone via line 56. The product alkanolamine is withdrawn from the reboiler via line 54.

The preferred product output comprises the alkanolamine selected from the group consisting of a monoalkanolamine, a dialkanolamine, and a trialkanolamine. In one embodiment, the product output comprises a mixture of at least two alkanolamines selected from the group consisting of a monoalkanolamine, a dialkanolamine, and a trialkanolamine. In another preferred embodiment, the product output consists essentially of dialkanolamine. Preferably, the product output comprises at least 75% by weight of the alkanolamine, more preferably, the product output comprises at least 85% by weight of the alkanolamine, and most preferably, the product output consists essentially of the alkanolamine. In addition, in certain embodiments, the mixture consists of at least 99.9% of the monoalkanolamine and the dialkanolamine with a balance being the trialkanolamine.

The process of the present invention also comprises producing the monoalkanolamine and the dialkanolamine at a product molar ratio of the monoalkanolamine to the dialkanolamine from about 0.071 to about 1.754.

Figure 2:
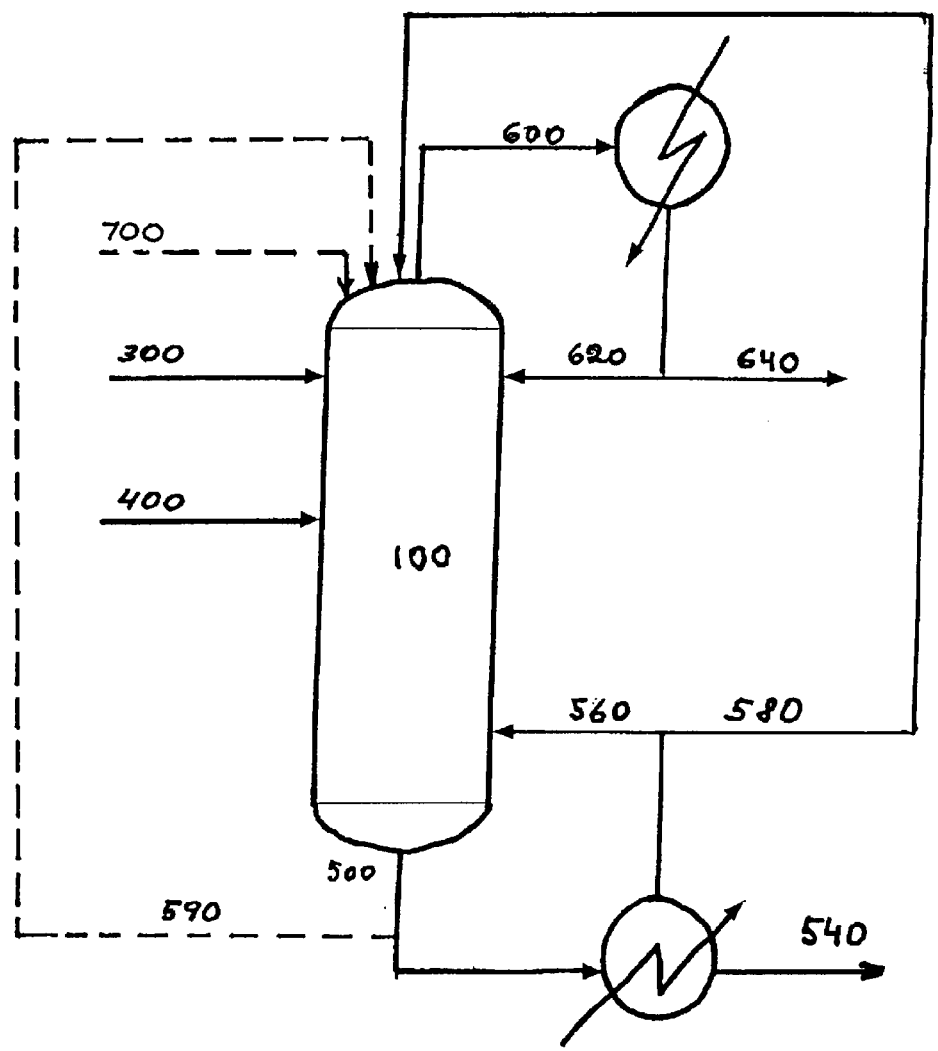
FIG. 2 illustrates a flow diagram for another embodiment of the process of this invention, wherein a part of a product output is recycled back to the apparatus to be used as a catalyst.

Also, when the product alkanolamine is being used as a catalyst, a portion of the product alkanolamine is recycled in the column, wherein it is directed either via line 590 (shown as a dashed line in FIG. 2) or line 580 to the overhead portion of the column 100, as shown in FIG. 2.

The preferred design and operating parameters of the reactive distillation column in the aqueous phase using water as a catalyst are selected as follows: (1) both feed amine and alkylene oxide are introduced in trays where the temperature is close to the desired reaction temperature (e.g., within about 305° K to about 573° K); (2) the product alkanolamine is withdrawn from a reboiler; (3) water used as a catalyst is mostly contained within the column and a part of it is removed from the bottom portion of the column along with the product alkanolamine; (4) the condensate stream containing water, an unreacted amine, and alkylene oxide (if any) is recycled back to the distillation column to obtain a high (e.g., from about above 1.1 to about 300) amine to alkylene oxide ratio in the column; and (5) the reboiler temperature is limited to a temperature that is substantially below the thermal degradation temperature of the product alkanolamine (e.g., within about 375° K to about 673° K). It is also desired to use one or more feed points for introducing the amine and/or the alkylene oxide into the column to prevent any chances of the alkylene oxide accumulating in the column and creating an hazardous environment.

In another embodiment of the present invention, the desired alkanolamine or a mixture of alkanolamines is produced in a reactive distillation column in a non-aqueous phase by reacting an amine, e.g., ammonia, with an alkylene oxide in the presence of a product alkanolamine as a catalyst. This process is illustrated in FIG. 2, wherein the product alkanolamine is directed from the bottom of the column 100 to the reboiler via line 500. A portion of the product is recycled from the reboiler via line 520 to bottom portion of the column 100 and line 580 to the overhead portion of the column 100. Optionally, product alkanolamine can be directed to the overhead portion of the column 100 via line 590 (shown here as a dashed line) as a part of the bottom output.

The reaction between the amine and the alkylene oxide occurs in a liquid phase, producing the desired product alkanolamine. The unreacted portion of reactants, which is mostly the unreacted amine is refluxed or recycled back to the column. Close to a total reflux is achieved when the unreacted amine, and alkylene oxide (if any) are removed in a gaseous state via line 600, condensed and returned to the column 100 via line 620. An optional purge line 640 is provided to regulate the reflux.

In another embodiment of the present invention, the desired product alkanolamine or a mixture of alkanolamines is produced in a reactive distillation column in the aqueous phase using both water and the product alkanolamine as catalysts, wherein an amine, e.g., ammonia is reacted with an alkylene oxide. This process is shown in FIG. 2, wherein water is introduced into the column 100 via line 700 (shown here as a dashed line). Similarly to the non-aqueous process, a portion of the product alkanolamine is recycled from the reboiler via line 580 or line 590 to the overhead portion of the column 100 to serve as a catalyst. However, in the aqueous process, water may be present in the recycle stream containing the product alkanolamine.

The preferred design and operating parameters of the reactive distillation column are selected as follows: (1) both feed amine and alkylene oxide are introduced in trays where the temperature is close to the desired reaction temperature (e.g., within about 305° K to about 573° K); (2) the product alkanolamine is withdrawn from the reboiler, (3) the reboiler temperature is limited to a temperature that is substantially below the thermal degradation temperature of the product alkanolamine (e.g., within 375° K to about 673° K); (4) the condensate stream containing an unreacted amine and the alkylene oxide (if any) is recycled back to the distillation column to obtain a high (e.g., from about above 1.1 to about 300) amine to alkylene oxide ratio in the column, and (5) a part of the product alkanolamine is recycled and introduced from the top portion of the column as a catalyst. It is also proposed to use one or more feed points for introducing amine (or ammonia) and/or alkylene oxide into the column to prevent any chances of alkylene oxide accumulating in the column and creating a hazardous environment.

Finally, besides saving capital and operating cost, the novel reactive distillation process provides a unique opportunity or flexibility of producing a wide variety of alkanolamines in the same plant, as will be evidenced in the Examples below.

The invention will be illustrated in more detail with reference to the following Examples, but it should be understood that the present invention is not deemed to be limited thereto.

Production of Isopropanolamines by Aqueous Phase Reactive Distillation

EXAMPLE 1

A novel one-step reactive distillation approach was employed to streamline and economize the production of isopropanolamines including mono-isopropanolamine (MIPLA), di-isopropanolamine (DIPLA), and tri-isopropanolamine (TIPLA). A mixture of ammonia and propylene oxide (PO) was reacted in a packed distillation column shown in FIG. 1 to produce isopropanolamines (IPLAs) by an aqueous phase reactive distillation. The production of IPLAs was simulated using a packed distillation column in the Aspen simulator. The packed reactive distillation column used in the simulation was 0.5 meter in diameter and had a height equivalent to theoretical plate (HETP) of 0.5 meter. The column had close to eight stages. It was operated at a total pressure of 13 bar (13 kPa) to keep a part of ammonia in the liquid phase. In addition, it was operated under a total reflux of the unreacted ammonia to achieve a high ratio of ammonia to PO in the column.

Liquid ammonia was introduced above the second stage of the packed reactive distillation column at a feed rate of 254 kg/hr. Liquid propylene oxide (PO) was also fed above the second stage at a feed rate of 1100 kg/hr. Water, needed to catalyze the reaction, was introduced above the first stage at a rate of 200 kg/hr. The condensate containing a mixture of ammonia, water and PO at 311° K, and was completely recycled back to the distillation column. The reaction zone temperatures ranged between 316° K and 323° K. The reaction product containing isopropanolamines and water was withdrawn from the bottom of the column for further processing and separation. The reboiler temperature was 463° K. The column had a total condenser and kettle reboiler duty of about 460 kW. The average residence time in the column was approximately 12 minutes.

The results from reactive distillation simulation showed that even though the molar ratio of ammonia to PO of 0.79:1 in the fresh feed was low, the process molar ratio of ammonia to PO in the column was higher and in the preferred range for producing the desired products. Due to the total reflux of unreacted ammonia, the ratio of ammonia to PO in the column ranged from 5:1 to 30:1. The simulation results also showed that the overall molar conversion of PO was 99.96%. More importantly, being close to 99.5% of converted PO resulted in producing predominantly IPLAs. The final product contained 61.3% MIPLA, 35.1% DIPLA and 3.6% TIPLA. The molar ratio of MIPLA to DIPLA in the product was 1.75:1.

This example showed that the extremely high conversion of PO to IPLAs could be obtained by using the reactive distillation technique even with the use of the initial low molar ratio of ammonia to PO in the fresh feed mixture. The example also showed that the reactive distillation technique could be used to maximize the production of more desirable MIPLA and DIPLA and minimize the production of less desirable TIPLA.

EXAMPLES 2 TO 6

The production of IPLAs by the reactive distillation technique as described in Example 1 was repeated in Examples 2 to 6 using a similar reactive distillation column design, similar flow rates of ammonia, PO, and water, a similar operating pressure and temperature, and similar stages of introducing feed ammonia and water. Instead of introducing fresh PO above stage 2 as done in Example 1, the fresh feed PO was introduced above stages 3 to 7 in these examples to optimize the production of IPLAs, as shown in Table 1 below. The optimum production of IPLAs was judged based on the overall conversion of PO and the ratio of MIPLA to DIPLA in the final product.

The simulation results summarized in Table 1 showed that the reactive distillation technique was very effective in manipulating product distribution simply by changing the location of introducing the fresh feed PO into the column. The results also showed that it would not be desirable to introduce PO above trays 3 to 7 to increase the production of the desired product alkanolamine.

EXAMPLES 7 TO 12

The production of IPLAs by reactive distillation technique as described in Example 1 was repeated again in Examples 7 to 12 using a similar reactive distillation column design, similar flow rates of ammonia, PO, and water, a similar operating pressure and temperature, and a similar stage of introducing feed water. The feed ammonia was introduced in these examples above stage 3 instead of introducing above stage 2 as done in Example 1. The feed PO was introduced above stages 2 to 7 in these examples to optimize the production of IPLAs, as shown in Table 1 below. The optimum production of IPLAs was judged based on the overall conversion of PO and the ratio of MIPLA to DIPLA in the final product.

The simulation results summarized in Table 1 showed that the reactive distillation technique was very effective in manipulating the product distribution simply by changing locations of introducing feed PO and ammonia into the column. The results also showed that the production of desirable products could be increased by introducing PO above stage 2 and ammonia above stage 3.

EXAMPLES 13 TO 18

The production of IPLAs by the reactive distillation technique as described in Example 1 was repeated again in Examples 13 to 18 using a similar reactive distillation column design, similar flow rates of ammonia, PO, and water, a similar operating pressure and temperature, and a similar stage of introducing feed water. The feed ammonia was introduced in these examples above stage 4 instead of introducing above stage 2 as done in Example 1. The feed PO was introduced above stages 2 to 7 in these examples to optimize the production of IPLAs, as shown in Table 1 below. The optimum production of IPLAs was judged based on the overall conversion of PO and the ratio of MIPLA to DIPLA in the final product.

The simulation results summarized in Table 1 showed that the reactive distillation technique was very effective in manipulating the product distribution simply by changing locations of introducing feed PO and ammonia into the column. The results also showed that the production of desirable products could be increased by introducing PO above stage 2 and ammonia above stage 4.

EXAMPLES 19 TO 24

The production of IPLAs by the reactive distillation technique as described in Example 1 was repeated again in Examples 19 to 24 using a similar reactive distillation column design, similar flow rates of ammonia, PO, and water, a similar operating pressure and temperature, and a similar stage of introducing feed water. The feed ammonia was introduced in these examples above stage 5 instead of introducing above stage 2 as done in Example 1. The feed PO was introduced above stages 2 to 7 in these examples to optimize the production of IPLAs, as shown in Table 1 below. The optimum production of IPLAs was, once again, judged based on the overall conversion of PO and the ratio of MIPLA to DIPLA in the final product.

The simulation results summarized in Table 1 showed that that the reactive distillation technique was very effective in manipulating product distribution simply by changing locations of introducing feed PO and ammonia into the column. The results also showed that the production of desirable products could be increased by introducing PO above stage 2 and ammonia above stage 5.

TABLE 1

Effect of Feed Tray Location on Product Distribution

| Example No. | $NH_3$ Feed Stage | PO Feed Stage | MIPLA / DIPLA | PO Conversion % | Temperature of Condenser °K. |
|---|---|---|---|---|---|
| 1 | 2 | 2 | 1.75 | 99.99+ | 311.5 |
| 2 | 2 | 3 | 1.57 | 99.99+ | 310.1 |
| 3 | 2 | 4 | 1.34 | 99.99+ | 309.8 |
| 4 | 2 | 5 | 1.07 | 99.99 | 309.6 |
| 5 | 2 | 6 | 0.86 | 99.98 | 309.6 |
| 6 | 2 | 7 | 0.74 | 99.91 | 309.6 |
| 7 | 3 | 2 | 1.74 | 99.99+ | 311.7 |
| 8 | 3 | 3 | 1.57 | 99.99+ | 310.2 |
| 9 | 3 | 4 | 1.34 | 99.99+ | 309.8 |
| 10 | 3 | 5 | 1.07 | 99.99 | 309.6 |
| 11 | 3 | 6 | 0.86 | 99.97 | 309.6 |
| 12 | 3 | 7 | 0.74 | 99.91 | 309.6 |
| 13 | 4 | 2 | 1.72 | 99.99+ | 311.8 |
| 14 | 4 | 3 | 1.57 | 99.99+ | 310.2 |
| 15 | 4 | 4 | 1.34 | 99.99+ | 309.8 |
| 16 | 4 | 5 | 1.07 | 99.99 | 309.6 |
| 17 | 4 | 6 | 0.86 | 99.97 | 309.6 |
| 18 | 4 | 7 | 0.74 | 99.91 | 309.6 |
| 19 | 5 | 2 | 1.69 | 99.99+ | 311.8 |
| 20 | 5 | 3 | 1.56 | 99.99+ | 310.2 |
| 21 | 5 | 4 | 1.34 | 99.99+ | 309.8 |
| 22 | 5 | 5 | 1.07 | 99.99 | 309.6 |
| 23 | 5 | 6 | 0.86 | 99.97 | 309.6 |
| 24 | 5 | 7 | 0.74 | 99.91 | 309.6 |

EXAMPLES 25 TO 33

The production of IPLAs by the reactive distillation technique as described in Example 2 was repeated in Examples 25 to 31 using a similar reactive distillation column design similar flow rates and feed locations of ammonia, PO, and water. Instead of operating the column at 13 bar (13 kPa) total pressure, the column operating pressure was varied between 12 and 20 bar (12 and 20 kPa) to optimize the production of IPLAs, as shown in Table 2 below. The optimum production of IPLAs was judged based on the overall conversion of PO and the molar ratio of MIPLA to DIPLA in the final product.

TABLE 2

Effect of Operating Pressure on Production Distribution

| Example | Operating Pressure (bar) | MIPLA/ DIPLA | PO Conversion % | Temperature of Condenser, °K. |
|---|---|---|---|---|
| 25 | 12 | 1.42 | 99.88 | 307.3 |
| 26 | 13 | 1.57 | 99.96 | 310.1 |
| 27 | 14 | 1.68 | 99.98 | 312.8 |
| 28 | 15 | 1.75 | 99.99 | 315.3 |
| 29 | 16 | 1.81 | 99.99+ | 317.7 |
| 30 | 17 | 1.86 | 99.99+ | 319.9 |
| 31 | 18 | 1.89 | 99.99+ | 322.1 |
| 32 | 19 | 1.91 | 99.99+ | 324.1 |
| 33 | 20 | 1.92 | 99.99+ | 326.1 |

The simulation results summarized in Table 2 showed that the desired ratio of co-products (MIPLA/DIPLA) could be increased by simply increasing the operating pressure of the reactive distillation column.

Production of Dimethylethanolamine by Aqueous Phase Reactive Distillation

EXAMPLE 34

A novel one-step reactive distillation approach was employed to streamline and economize the production of dimethylethanolamine (DMEA). A mixture of dimethylamine (DMA) and ethylene oxide (EO) was reacted in a packed distillation column to produce dimethylethanolamine (DMEA) by aqueous phase reactive distillation. The production of DMEA was simulated by using a packed distillation column in the Aspen simulator. The packed reactive distillation column used in the simulation was 1 meter in diameter and had a HETP of 0.5 meter. The column had close to eight stages. It was operated at a total pressure of 2.5 bar (2.5 kPa) to keep a part of DMA in the liquid phase. In addition, it was operated under a total reflux of the unreacted DMA to maintain a high DMA to EO ratio in the column.

Liquid DMA was introduced above the third stage of the packed reactive distillation column at a feed-rate of 1146 kg/hr. Liquid ethylene oxide (EO) was also fed above the third stage at a feed-rate of 1100 kg/hr. Water, needed to catalyze the reaction, was added above the first stage at a rate of 200 kg/hr.

The condensate containing a mixture of ammonia, water and EO at 305° K was completely recycled back to the column to achieve a high DMA to EO ratio in the column. The reaction zone temperatures ranged between 305° K and 314° K. The reaction product containing DMEA and water was withdrawn from the bottom of the column for further processing and separation. The reboiler temperature of 427° K was maintained by a duty of 800 kW. Average residence time in the column was 12 minutes.

The reactive distillation simulation results showed that even though the molar ratio of DMA to EO of 1:1 in the fresh feed was low, the process molar ratio of DMA to EO in the column was high and in the preferred range for producing the desired product. Due to total reflux of the unreacted portion of DMA, the process molar ratio of DMA to EO in the column ranged from 20:1 to 110:1. The simulation results showed that the overall molar conversion of EO was 99.99%.

This example showed that an extremely high conversion of EO to DMEA could be obtained by using the reactive distillation technique even with the use of the initial low molar ratio of DMA to EO in the feed.

Production of Dimethylethanolamine by Non-Aqueous Phase Reactive Distillation

EXAMPLE 35

A novel one-step reactive distillation approach was employed to streamline and economize the production of dimethylethanolamine (DMEA) by non-aqueous phase reactive distillation. A mixture of DMA and EO was reacted in a packed distillation column to produce dimethylethanolamine by the non-aqueous phase reactive distillation. The production of DMEA was simulated by using a packed distillation column model in the Aspen simulator. The packed reactive distillation column used in the simulation was 0.5 meter in diameter and had a HETP of 0.5 meter. The column had close to six stages. The column was operated at a total pressure of 5 bar (5 kPa) pressure to keep a part of DMA in the liquid phase. In addition, the column was operated under a total reflux of the unreacted portion of DMA to maintain a high DMA to EO ratio in the column.

Liquid DMA was introduced on the second stage of the packed reactive distillation column at a feed-rate of 1140 kg/hr. Liquid EO was also fed on the second stage at a feed-rate of 1101 kg/hr. Liquid DMEA, needed as a catalyst, was added above the first stage at a feed-rate of 19 kg/hr. The condensate containing DMA at 337° K was completely recycled back to achieve a high DMA to EO ratio in the column. The reaction occurred on the feed stage at 419° K. The reaction product comprised of DMEA was withdrawn from the bottom of the column. A temperature of about 463° K was maintained in the reboiler kettle. Average residence time in the column was under 2 minutes.

The reactive distillation simulation results showed that even though the molar ratio of DMA to EO of 1:1 in the fresh feed was low, the process molar ratio of DMA to EO in the column was high and in the preferred range for producing the desired product. Due to the total reflux of the unreacted portion of DMA, the process molar ratio of DMA to EO in the column was greater than 100:1. The simulation results also showed that the overall molar conversion of EO was 99.99%.

This example showed that the extremely high conversion of EO to DMEA could be obtained by using the reactive distillation technique even with the use of the initial low molar ratio of DMA to EO in the feed mixture.

Production of Diethylethanolamine by Aqueous Phase Reactive Distillation

EXAMPLE 36

A novel one-step reactive distillation approach was employed to streamline and economize the production of diethylethanolamine (DEEA). A mixture of diethylamine (DEA) and ethylene oxide (EO) was reacted in a packed distillation column to produce diethylethanolamines by aqueous phase reactive distillation. The production of DEEA was simulated by using a packed distillation column in the Aspen simulator. The packed reactive distillation column used in the simulation was 0.75 meter in diameter and had a HETP of 0.5 meter. The column had close to eight stages. It was operated at a total pressure of 2 bar (2 kPa) to keep a part of DEA in the liquid phase. In addition, it was operated under a total reflux of the unreacted portion of diethylamine to maintain a high molar ratio DEA to EO in the column.

Liquid DEA was introduced on the second stage of the packed reactive distillation column at a feed-rate of 2011 kg/hr. Liquid EO was fed above the fourth stage at a feed-rate of 1101 kg/hr. Water, needed to catalyze the reaction, was introduced above the first stage at a rate of 200 kg/hr. The condensate containing a mixture of DEA, water and EO at 356K was completely recycled back to achieve a high DEA to EO ratio in the column. The liquid phase reaction took place on a series of stages in a temperature range between 359° K to 368° K. The reaction product containing DEEA and water was withdrawn from the bottom of the column for further processing and separation. The kettle reboiler temperature was maintained at 375° K with a 200 kW duty. The average column residence time was approximately 7 minutes.

The reactive distillation simulation results showed that even though the molar ratio of DEA to EO of 1.1:1 in the fresh feed was low, the process molar ratio of diethylamine to ethylene oxide in the column was high and in the preferred range for producing the desired product. Due to the total reflux of the unreacted portion of DEA, the molar ratio of DEA to EO in the column ranged from 1.5:1 to over 100:1. The simulation results also showed that the overall molar conversion of EO was 99.95%. More importantly, close to 99.6% of EO fed to the column was consumed to produce DEEA.

This example showed that an extremely high conversion of EO to DEEA could be obtained by using the reactive distillation technique even using the initial low molar ratio of DEA to EO in the feed.

Production of Diethylethanolamine by Non-Aqueous Phase Reactive Distillation

EXAMPLE 37

A novel one-step reactive distillation approach was employed to streamline and economize the production of DEEA by a non-aqueous phase reactive distillation using DEA and EO. The production of DEEA was simulated by using a packed distillation column in the Aspen simulator. The packed reactive distillation column used in the simulation was 1.0 meter in diameter and had a HETP of 0.5 meter. The column had close to eight stages. It was operated at a total pressure of 2 bar (2 kPa) to keep a part of DEA in the liquid phase. In addition, it was operated under a total reflux of the unreacted portion of diethylamine to maintain a high molar ratio of DEA to EO in the column.

Liquid DEA was introduced on the second stage of the packed reactive distillation column at a feed-rate of 2011 kg/hr. Liquid ethylene oxide was fed above the fourth stage at a feed-rate of 1101 kg/hr. Liquid DEEA, needed to catalyze the reaction, was introduced above the first stage at a rate of 19 kg/hr. The condensate containing primarily diethylamine at 350° K was completely recycled to achieve a high molar ratio of DEA to EO in the column. The liquid phase reaction took place on a series of stages in a temperature range between 351° K to 386° K. The reaction product containing DEEA and the unreacted portion of DEA was withdrawn from the bottom of the column for further processing and separation. The kettle reboiler temperature was maintained at 439° K with a 200 kW duty. The average column residence time was approximately 8 minutes.

The reactive distillation simulation results showed that even though the initial molar ratio of DEA to EO of 1.1:1 in the fresh feed was low, the process molar ratio of DEA to EO in the column was high and in the preferred range for producing the desired product. Due to the total reflux of the unreacted portion of DEA, the process molar ratio of DEA to EO in the column ranged from 35:1 to over 200:1. The simulation results also showed that the overall molar conversion of EO was greater than 99.99%.

This example therefore showed that an extremely high conversion of EO to DEEA could be obtained by using the reactive distillation technique even with the use of the initial low molar ratio of DEA to EO in the feed.

Production of Methylethanolamines by Aqueous Phase Reactive Distillation

EXAMPLE 38

A novel one-step reactive distillation approach was employed to streamline and economize the production of methylethanolamine (M11), methyldiethanolamine (M12) and methyltriethanolamine (M13). A mixture of monomethylamine (MMA) and ethylene oxide (EO) was reacted in a packed distillation column to produce methylethanolamines by the aqueous phase reactive distillation. The production of methylethanolamines was simulated by using a packed distillation column in the Aspen simulator. The packed reactive distillation column used in the simulation was 0.5 meter in diameter and had a HETP of 0.5 meter. The column had close to eight stages. It was operated at a total pressure of 10 bar (10 kPa) to keep a part of the MMA in the liquid phase. In addition, it was operated under a total reflux of the unreacted portion of MMA to maintain a high molar ratio of MMA to EO in the column.

Liquid MMA was introduced above the second stage of the packed reactive distillation column at a feed-rate of 457 kg/hr. Liquid EO was also fed above the second stage at a feed-rate of 1100 kg/hr. Water, needed to catalyze the reaction, was added above the first stage at a rate of 200 kg/hr. The condensate containing a mixture of MMA, water and EO at 336° K was completely recycled to achieve a high process molar ratio of MMA to EO in the column. The reaction occurred within a temperature range between 336° K and 345° K. The kettle reboiler temperature of 485° K was maintained with a duty of 600 kW. The average residence time in the column was 12 minutes.

The reactive distillation simulation results showed that even though the initial molar ratio of MMA to EO of 0.59:1 in the fresh feed was low, the process molar ratio of MMA to EO in the column was high and in the preferred range for producing the desired products. Due to total reflux of the unreacted portion of MMA, the process molar ratio of MMA to EO in the column ranged from 10:1 to greater than 40:1. The simulation results also showed that the overall molar conversion of EO was 99.97%. More importantly, close to 99.96% of EO fed to the column resulted in producing methylethanolamines. The final product contained 16.7% M11, 83.3% M12, and a trace amount of M13. The molar ratio of M12 to M11 in the product output was 5.0.

This example therefore showed that an extremely high conversion of EO to methylethanolamines could be obtained by using the reactive distillation technique even using the low molar ratio of MMA to EO in the feed. The example also showed that the reactive distillation technique could be used to increase the production of the more desirable M12 and M11 and to reduce the production of the less desirable M13.

EXAMPLE 39 TO 43

The production of methylethanolamines by the reactive distillation technique described in Example 38 was repeated in Examples 39 to 43 using a similar reactive distillation column design, similar flow rates of monomethylamine, EO and water, a similar operating pressure and temperature, and similar stages of introducing MMA, the reactant, and water, the catalyst. Instead of introducing EO above stage 2 as done in Example 38, EO, the reactant, was introduced above stages 3 to 7 in these examples to optimize the production of the methylethanolamines. The optimum production of the methylethanolamines was judged based on the overall conversion of EO and the molar ratio of M12 to M11 in the product output.

The simulation results summarized in Table 3 showed that the reactive distillation technique was very effective in manipulating the product distribution simply by changing a location of introducing the fresh feed EO into the column. The results also showed that it would be desirable to introduce EO above trays 3 to 7 to increase production of the desired products, e.g., to increase production of M12 over M11.

TABLE 3

Effect of Feed Tray Location on Product Distribution

| Example No. | EO Feed Stage | Molar Ratio M12/M11 | EO Conversion % | Temperature of Condenser ° K. |
|---|---|---|---|---|
| 38 | 2 | 5.0 | 99.93 | 336.5 |
| 39 | 3 | 5.13 | 99.98 | 335.1 |
| 40 | 4 | 5.62 | 99.99 | 334.8 |
| 41 | 5 | 6.92 | 99.99+ | 334.7 |

TABLE 3-continued

Effect of Feed Tray Location on Product Distribution

| Example No. | EO Feed Stage | Molar Ratio M12/M11 | EO Conversion % | Temperature of Condenser ° K. |
|---|---|---|---|---|
| 42 | 6 | 9.79 | 99.99+ | 334.7 |
| 43 | 7 | 14.0 | 99.98 | 334.6 |

Production of Methylethanolamines by a Non-Aqueous Phase Reactive Distillation

EXAMPLE 44

A novel one-step reactive distillation approach was employed to streamline and economize the production of M11, M12, and M13. A mixture of monomethylamine (MMA) and ethylene oxide (EO) was reacted in a packed distillation column to produce methylethanolamines by a non-aqueous phase reactive distillation. The production of methylethanolamines was simulated by using a packed distillation column in an Aspen simulator. The packed reactive distillation column used in the simulation was 0.5 meter in diameter and had a HETP of 0.5 meter. The column had close to eight stages. It was operated at a total pressure of 12 bar pressure to keep a part of the MMA in the liquid phase. In addition, it was operated under total reflux of the unreacted portion of MMA to maintain a high process molar ratio of MMA to EO in the column.

Liquid MMA was introduced on the sixth stage of the packed reactive distillation column at a feed-rate of 683 kg/hr. Liquid EO was fed above the second stage at a feed-rate of 1101 kg/hr. Liquid M11, needed to catalyze the reaction, was added above the first stage at a rate of 19 kg/hr. The condensate containing MMA at 340° K was completely recycled to achieve a high molar ratio of MMA to EO in the column. The reaction occurred at 350° K in the column. The kettle reboiler temperature of 467° K was maintained with a duty of 678 kW. The average residence time in the column was 7 minutes.

The reactive distillation simulation results showed that even though the initial molar ratio of MMA to EO of 0.88:1 in fresh feed was low, the process molar ratio of MMA to EO in the column was high and in the preferred range for producing the desired products. Due to the total reflux of the unreacted portion of MMA, the process molar ratio of MMA to EO in the column was greater than 90:1. The simulation results also showed that the overall molar conversion of EO was 99.99%. The final product contained 63.5% M11 (2-methylaminoethanol), 36.4% M12 (methyldiethanolamine) and 0.02% M13 (methyltriethanolamine). The ratio of M11 to M12 in the product was 1.74:1.

This example showed that an extremely high conversion of EO to methylethanolamines could be obtained by using the reactive distillation technique even using a low molar ratio of MMA to EO in the feed. The example also showed that the reactive distillation technique could be used to increase the production of the more desirable M12 and M11 and to reduce the production of the less desirable M13.

EXAMPLES 45 TO 47

The production of methylethanolamines by the reactive distillation technique described in Example 44 was repeated in Examples 45 to 47 using a similar reactive distillation column design, similar flow rates of monomethylamine and EO, a similar operating pressure and temperature, and similar stages of introducing MMA, the reactant, and M11, the catalyst. Instead of introducing EO above stage 2 as done in Example 47, the feed EO was introduced above stages 3 to 5 in these examples to optimize the production of methylethanolamines. The optimum production of methylethanolamines was judged based on the overall conversion of EO and the molar ratio of M12 to M11 in the final product output.

The simulation results summarized in Table 4 showed that the reactive distillation technique was very effective in manipulating the product distribution simply by changing a location of introducing the fresh feed EO into the column. It was discovered that the relative amounts of M12 and M13 to M11 change dramatically with the change of the EO feed location. The EO feed stage located high in the column produces mostly M11. The EO feed stage located lower in the column produces a M12 rich product with higher amounts of M13. The results also showed that it would be desirable to introduce EO above trays 3 to 5 to increase production of the desired products, e.g., to increase production of M12 over M11.

TABLE 4

Effect of Feed Tray Location on Product Distribution

| Example No. | EO Feed Stage | M12/M11 Molar Ratio | M13/M11 Molar Ratio | EO Conversion % | Temperature of Condenser ° K. |
|---|---|---|---|---|---|
| 44 | 2 | 0.57 | <0.0003 | 99.99 | 339.5 |
| 45 | 3 | 3.46 | 0.9 | 99.99+ | 339.5 |
| 46 | 4 | 3.42 | 1.2 | 99.99+ | 339.5 |
| 47 | 5 | 3.31 | 1.1 | 99.99+ | 339.5 |

These examples therefore showed that the extremely high conversion of EO to methylethanolamines could be obtained by using the reactive distillation technique even though the ratio of MMA in the feed was low. The example also showed that the reactive distillation technique could be used to increase the production of the more desirable M12 and M11 and to decrease the production of the less desirable M13.

Ethanolamines Production by Aqueous Phase Reactive Distillation

EXAMPLE 48

Ethanolamines such as mono-ethanolamine (MELA), di-ethanolamine (DELA) and tri-ethanolamine (TELA) are produced by reacting ethylene oxide (EO) with an excess amount of ammonia. A novel one-step reactive distillation approach was employed to streamline and economize the production of MELA and DELA by an aqueous phase reactive distillation, wherein a mixture of reactants, ammonia and ethylene oxide (EO), was reacted in a packed distillation column to produce ethanolamines. The production of ethanolamines was simulated by using a packed distillation column in the Aspen simulator. The packed reactive distillation column used in the simulation was 0.35 meter in diameter and had a HETP of 0.5 meter. The column had close to eight stages. It was operated at a total pressure of 17 bar (17 kPa) to keep a part of the ammonia in the liquid phase. In addition, it was operated under a total reflux of an unreacted part of ammonia to maintain a high molar ratio of ammonia to EO in the column. Water was used to catalyze the reaction.

The liquid ammonia was introduced above the sixth stage of the packed reactive distillation column at a feed-rate of 225 kg/hr. The liquid ethylene oxide (EO) was fed above the second stage at a feed-rate of 834 kg/hr. Water was added above the first stage at a rate of 200 kg/hr. The condensate containing a mixture of ammonia, water and EO at 322° K was completely recycled to achieve the high ammonia to EO molar ratio in the column. The reaction occurred in a temperature range between 322° K and 350° K. The reaction product output containing ethanolamines and water was withdrawn from the bottom of the column for further processing and separation. The reboiler temperature of 501° K was maintained with a duty of 350 kW. The average residence time in the column was 15 minutes.

The reactive distillation simulation results showed that even though the initial molar ratio of ammonia to EO of 0.7:1 in the fresh feed was low, the process molar ratio of ammonia to EO in the column was high and in the preferred range for producing the desired products. Due to the total reflux of the unreacted portion of ammonia, the process molar ratio of ammonia to EO in the column ranged from 7:1 to 50:1. The simulation results also showed that the overall molar conversion of EO was 99.96%. More importantly, 99.5% of EO fed was consumed to produce ethanolamines. The final product contained 52.1% MELA, 40.2% DELA and 7.7% TELA. The ratio of MELA to DELA was 1.3:1.

This example therefore showed that the extremely high conversion of EO to ethanolamines could be obtained by using the reactive distillation technique even with the use of the low molar ratio of ammonia to EO in the feed. The example also showed that the reactive distillation technique could be used to manipulate the relative ratio of ethanolamines, e.g., MELA and DELA.

EXAMPLES 49 TO 52

The production of ethanolamines by the reactive distillation technique described in Example 48 was repeated in Examples 49 to 52 using a similar reactive distillation column design, similar flow rates of ammonia, EO and water, a similar operating pressure and temperature, and similar stages of introducing feed ammonia and water.

Instead of introducing EO above the stage 2 as done in Example 48, the feed EO was introduced above stages 3 to 6 to optimize the production of ethanolamines. The optimum production of ethanolamines was judged based on the overall conversion of EO and the molar ratio of MELA to DELA in the final product output.

The simulation results summarized in Table 5 show that the reactive distillation technique was very effective in manipulating the product distribution simply by changing the location of introducing the fresh feed EO into the column.

TABLE 5

Effect of feed tray location on product ratio

| Example No. | EO feed Stage | MELA/ DELA Molar Ratio | MELA/TELA Molar Ratio | EO Conversion (%) | Condenser Temperature (° K.) |
|---|---|---|---|---|---|
| 48 | 2 | 1.29 | 6.8 | 99.96 | 322.8 |
| 49 | 3 | 1.29 | 6.8 | 99.99 | 320.2 |
| 50 | 4 | 1.27 | 6.9 | 99.99+ | 319.7 |
| 51 | 5 | 1.18 | 6.8 | 99.99+ | 319.5 |
| 52 | 6 | 0.98 | 5.0 | 99.99+ | 319.5 |

EXAMPLE 53 TO 59

The production of ethanolamines by the reactive distillation technique described in Example 48 was repeated in Examples 53 to 59 using a similar reactive distillation column design, similar flow rates of ammonia, EO and water, and similar stages of introducing feed ammonia and water. Instead of operating the column at 17 bar pressure as done in Example 48, the column operating pressure was varied between 14 and 21 bar. The optimum production of ethanolamines was judged based on the overall conversion of EO and ratios of MELA to DELA and MELA to TELA in the final product.

The results shown in Table 6 illustrate that the relative ratios of MELA to DELA and MELA to TELA can be manipulated simply by changing the column pressure.

TABLE 6

Effect of Operating Pressure on Product Distribution

| Example No. | Pressure (Bar) | MELA/ DELA Molar Ratio | MELA/ TELA Molar Ratio | EO Conversion (%) | Condenser Temperature (° K.) |
|---|---|---|---|---|---|
| 53 | 14 | 1.34 | 7.78 | 99.94 | 315.6 |
| 54 | 15 | 1.33 | 7.42 | 99.95 | 318.1 |
| 55 | 16 | 1.31 | 7.09 | 99.95 | 320.5 |
| 48 | 17 | 1.29 | 6.8 | 99.96 | 322.8 |
| 56 | 18 | 1.28 | 6.5 | 99.96 | 324.9 |
| 57 | 19 | 1.26 | 6.23 | 99.97 | 326.9 |
| 58 | 20 | 1.25 | 5.98 | 99.97 | 328.9 |
| 59 | 21 | 1.23 | 5.73 | 99.97 | 330.7 |

While the invention has been described in detail and with reference to specific examples thereof, it will be apparent to one skilled in the art that various changes and modifications can be made therein without departing from the spirit and scope thereof.

What is claimed is:

1. A process for producing an alkanolamine, said process comprising:

supplying a reactive distillation apparatus, wherein the reactive distillation apparatus has an inner contacting surface and the inner contacting surface facilitates simultaneously a reaction process and a distillation process;

feeding to the reactive distillation apparatus a first reactant, the first reactant comprising an amine represented by $R'_{3-x}NH_x$, wherein R' is a hydrocarbon group, and X is 1, 2, or 3;

feeding to the reactive distillation apparatus a second reactant, the second reactant comprising an alkylene oxide represented by R"O, wherein R" is a $C_2$–$C_{10}$-alkylene;

feeding to the reactive distillation apparatus a catalyst, wherein the catalyst is provided in an amount from 0% to about 15% by weight of a mixture of the first reactant, the second reactant and the catalyst;

recycling an overhead output from an overhead portion of the reactive distillation apparatus, the overhead output comprising an unreacted portion of the amine and the catalyst, wherein the overhead output is returned to the reactive distillation apparatus to achieve a substantially total reflux of the amine and the catalyst; and collecting a product output from a bottom portion of the reactive distillation apparatus, wherein the product output comprises the alkanolamine, the alkanolamine comprising at least one member selected from the group consisting of a monoalkanolamine, a dialkanolamine, and a trialkanolamine.

2. The process according to claim 1, wherein the product output comprises at least 75% by weight of the alkanolamine.

3. The process according to claim 1, wherein the product output comprises at least 85% by weight of the alkanolamine.

4. The process according to claim 1, wherein the product output consists essentially of the alkanolamine.

5. The process according to claim 1, wherein R' in the amine is a $C_1$–$C_{24}$-alkyl.

6. The process according to claim 1, wherein R' in the amine is a $C_1$–$C_4$-alkyl.

7. The process according to claim 1, wherein the amine is ammonia.

8. The process according to claim 1, wherein the amine is monomethylamine.

9. The process according to claim 1, wherein the amine is dimethylamine.

10. The process according to claim 1, wherein the amine is diethylamine.

11. The process according to claim 1, wherein the akylene oxide is a member selected from the group of consisting of ethylene oxide, propylene oxide, butylene oxide, and hexylene oxide.

12. The process according to claim 1, wherein the catalyst comprises at least one of water and the alkanolamine.

13. The process according to claim 1, wherein the catalyst is the product output.

14. The process according to claim 1, wherein an initial molar ratio of the first reactant to the second reactant ranges from about 0.1 to about 1.1, wherein the initial molar ratio is measured outside of the reactive distillation apparatus.

15. The process according to claim 14, wherein a process molar ratio of the first reactant to the second reactant ranges from about 1.1 to about 300, wherein the process molar ratio is measured inside of the reactive distillation apparatus.

16. The process according to claim 15, wherein the process molar ratio of the first reactant to the second reactant ranges from about 5 to about 200.

17. The process according to claim 1, wherein the process is conducted at a pressure of about 0.1 bar to about 100 bar (about 0.1 kPa to about 100 kPa).

18. The process according to claim 17, wherein the pressure is about 1 bar to about 100 bar (about 1 kPa to about 100 kPa).

19. The process according to claim 1, wherein the alkanolamine is represented by $R'_{3-X}NR'''_{X}$, wherein X is 1, 2, or 3 respectively, R' is a hydrocarbon group, and R''' is a $C_2$–$C_{10}$-alkanol group having at least one hydroxyl group.

20. The process according to claim 19, wherein R' is a $C_1$–$C_{24}$-alkyl.

21. The process according to claim 19, wherein the alkanolamine is selected from the group consisting of isopropanolamine, ethanolamine, methylethanolamine, dimethylethanolamine, and diethylethanolamine.

22. The process according to claim 1, wherein the alkylene oxide is completely reacted with the first reactant.

23. The process according to claim 1, wherein the contacting surface comprises at least one distillation tray.

24. The process according to claim 1, wherein the contacting surface comprises at least one of a structural packing and a dumped packing.

25. The process according to claim 1 conducted at a reaction temperature of about, 305° K to about 573° K.

26. The process according to claim 1, wherein the product output comprises a mixture of a monoalkanolamine, a dialkanolamine, and a trialkanolamine.

27. The process according to claim 26, wherein the mixture comprises at least 99.9% of the monoalkanolamine and the dialkanolamine with a balance being the trialkanolamine.

28. The process according to claim 27, wherein the monoalkanolamine and the dialkanolamine are produced at a product molar ratio of the monoalkanolamine to the dialkanolamine from about 0.071 to 1.754.

29. The process according to claim 28, wherein the product molar ratio is decreased by feeding to the reactive distillation apparatus the first reactant at a first feed point and by feeding the second reactant at a second feed point, wherein the second feed point is located at a distance below the first feed point.

30. The process according to claim 28, wherein the first reactant is fed to the reactive distillation apparatus at a first feed point and the second reactant is fed to the reactive distillation apparatus at a second feed point, wherein the second feed point is located at a distance above the first feed point.

31. The process according to claim 1, wherein the product output consists essentially of the dialkanolamine.

32. The process according to claim 1, wherein X is 1 or 2.

* * * * *